United States Patent [19]

Deghenghi

[11] Patent Number: 5,516,887
[45] Date of Patent: May 14, 1996

[54] LUTEINIZING HORMONE RELEASING HORMONE ANTAGONIST PEPTIDES

[75] Inventor: Romano Deghenghi, Chesaux Dessus B1, 1264 St. Cergue, Switzerland

[73] Assignee: Romano Deghenghi, St. Cergue, Switzerland

[21] Appl. No.: 140,045

[22] PCT Filed: Mar. 17, 1992

[86] PCT No.: PCT/EP92/00572

§ 371 Date: Jan. 17, 1994

§ 102(e) Date: Jan. 17, 1994

[87] PCT Pub. No.: WO92/19651

PCT Pub. Date: Nov. 12, 1992

[51] Int. Cl.$^6$ .............................. A61K 38/24; C07K 7/23
[52] U.S. Cl. ..................... 530/313; 530/327; 530/328
[58] Field of Search ..................... 530/313, 327, 530/328; 514/15, 16

[56] References Cited

U.S. PATENT DOCUMENTS

| | | | |
|---|---|---|---|
| 4,740,500 | 4/1988 | Vale, Jr. et al. | 514/15 |
| 4,800,191 | 1/1989 | Schally et al. | 514/15 |
| 4,801,577 | 1/1989 | Nestor, Jr. et al. | 514/15 |
| 4,851,385 | 7/1989 | Roeske | 514/15 |
| 5,003,011 | 3/1991 | Coy et al. | 530/328 |

FOREIGN PATENT DOCUMENTS

| | | |
|---|---|---|
| 0299402 | 1/1989 | European Pat. Off. . |
| 0413209 | 2/1991 | European Pat. Off. . |

OTHER PUBLICATIONS

S. Bajusz et al., "New Antagonists of LHRH", Int. J. Peptide Protein Res. 32:425 (1988).

J. A. Vilchez–Martinez et al., "Synthesis and Biological Properties of[Leu–6]–LH–RH and [D–LEU–6, DESG-LY–$NH_2^{10}$]–LH–RH Ethylamide", Biochem. Biophys. Res. Comun. 59(4):1226 (1974).

M. Fujino et al, "Structure–Activity Relationships in the C–Terminal Part of Luteinizing Hormone Releasing Hormone(LH–RH)", Biochem. Biophys. Res. Commun. 49(3):863 (1972).

A. S. Dutta et al., "Synthesis and Biological Activity of Highly Active α–Aza Analogues of Luliberin", J. Med. Chem. 21(10): 1018 (1978).

S. Bajusz et al., "Highly Potent Antagonists of Luteinizing Hormone–Releasing Hormone Free of Edematogenic Effects", Proc. Natl. Acad. Sci. USA 85:1637 (1988).

S. J. Hocart et al., "Effect of Reductive Alkylation of Lysine in Positions 6 and/or 8 on the Histamine-Releasing Activity of Luteinizing Hormone–Releasing Hormone Antagonists", 30(10):1910 (1987).

Primary Examiner—Christina Y. Chan
Assistant Examiner—Benet Prickril
Attorney, Agent, or Firm—Pennie & Edmonds

[57] ABSTRACT

A luteinizing hormone releasing hormone antagonist peptide is provided which effectively decreases plasma levels of estrogens and androgens. The peptide exhibits increased levels of potency while at the same time minimizing histamine releasing properties, vascular permeability (or edematogenic effects), hypotension, poor water solubility an inadequate duration of action associated with luteinizing hormone releasing hormone antagonist peptides of the past.

3 Claims, No Drawings

LUTEINIZING HORMONE RELEASING HORMONE ANTAGONIST PEPTIDES

TECHNICAL FIELD

This invention relates to novel peptide antagonists of luteinizing hormone.

BACKGROUND OF THE INVENTION

In the mammal, the anterior pituitary gland is located at the base of the brain, but is separate from it. A special set of closed circulation blood vessels connect the anterior pituitary to the brain at the region of the hypothalamus. It is the activity of the hypothalamus which largely regulates the production of luteinizing hormone, (LH), and follicle stimulating hormone, (FSH), by the anterior pituitary.

Within the hypothalamus, neurosecretory cells manufacture and release gonadotropic releasing hormones such as luteinizing hormone releasing hormone, (LHRH), also know as gonadotropic releasing hormone, (GnRH). LHRH enters a closed system of blood vessels directly connecting the hypothalamus with the anterior pituitary. As LHRH contacts neurosecretory cells located within the anterior pituitary these cells are stimulated to release luteinizing hormone into the systemic blood stream. In a similar manner, the hypothalamus causes the anterior pituitary to release FSH.

A developing mammalian egg, an oocyte grows to maturation within an ovarian follicle. Cyclically, the hypothalamus secretes follicle stimulating hormone releasing factor into the closed capillary system attaching the hypothalamus to the anterior pituitary. Once FSHRH contacts the anterior pituitary, it stimulates neurosecretory cells to produce FSH. FSH causes the mammalian follicle to grow both in size and number of cells. The follicle cells in turn secrete estrogen which stimulates the growth of the uterine wall in preparation for implantation of an embryo should fertilization occur. A feedback phenomenon occurs as estrogen level production stimulated by FSH rise causing both a direct reduction in the output of FSH by the anterior pituitary as well as an indirect effect by means of reducing hypothalamic stimulus of the anterior pituitary.

As the follicle reaches full maturity, the hypothalamus responds to the rising estrogen levels by secreting LHRH or luteinizing hormone releasing hormone into the closed capillary system connecting the hypothalamus with the anterior pituitary. As LHRH reaches the anterior pituitary, it stimulates release of luteinizing hormone. Luteinizing hormone stimulates the completion of maturation of the follicle and ovum. LH is also known as interstitial cell-stimulating hormone since it acts upon the interstitial cells of the testes in stimulating production of testosterone. After the mature follicle has released an ovum into the oviduct, the corpus luteum, which is derived from the remnant granulosa and theca cell of the ruptured follicle cells, becomes the equivalent of an endocrine gland secreting progesterone under the influence of LH.

If a fertilized egg is implanted, chorionic gonadotropin or CG is secreted by the placental tissues. CG prevents the corpus luteum from degenerating and allows it to continue its production of progesterone. Progesterone maintains the growth of cells of the endometrium as well as maintaining an adequate blood supply to nourish an implanted embryo.

Normally, as outlined above, the function of LH and FSH are biologically positive. FSH stimulates the mammalian follicle to produce estrogens while LH stimulates the corpus luteum to produce progesterone and the interstitial cells of the testes and ovaries to produce testosterone and estrogen respectively. FSH and LH have a synergism. That is to say, LH, when administered by itself has little or no effect, but combined with a small dose of FSH induces follicular maturation. Likewise, a small amount of LH greatly augments the response of the response of tissue to a small amount of FSH. For this reason, LHRH antagonists also affect the activity of FSH.

The above discussed hormones may be classified as gonadotropic as they stimulate growth and function of reproductive tissue. However, there are certain situations in which the gonadotropic effects of these hormones may deleteriously affect the health of an individual. Certain tumors derived of hormone dependent tissue are stimulated by the same gonadotropic hormones that stimulate healthy tissue. If such tumors are exposed to the normal anabolic effect of such hormones, rapid growth, and in the case of malignant tumors, metastasis is encouraged.

Various treatment modalities have been available for treating disease of hormone responsive tissue. Basically, these treatment modalities may be classified as those involving estrogen, androgen, and progestin additive therapy, or ablative procedures involving orchidectomy and removal of the ovaries.

Treatment of hormone dependent pathology such as uterine fibroids, breast, prostatic and testicular interstitial cancer, endometriosis and certain human papillomavirus associated tumors may be accomplished through altering the amount of circulating estrogen, progesterone, or testosterone. Precocious puberty may be treated by reducing the levels of circulating gonadotropic hormones.

Ablation, or castration therapy has been utilized in treating tumors derived from organs which are normally responsive, or dependent upon hormones. Ablative surgery has been used extensively in women with breast carcinoma. Removal of the ovaries is most beneficial to premenopausal women in whom there has been a long interval between mastectomy and recurrence or who have mainly osseous and soft-tissue metastases.

Orchidectomy has been utilized to treat carcinoma of the prostate. As with other ablative treatments, hormone therapy is sometimes used in place of excision. In prostate carcinoma, estrogen therapy has been utilized with some measure of success. Castration is especially effective in men with breast cancer and results in a response rate of nearly 70 percent. Thorn et al., *Harrison's Principles Of Internal Medicine*, eighth ed. pp. 1753, (1977).

Filicori et al., *GnRH Agonists and Antagonists Current Clinical Status*, Drugs 35:63–82 (1988) discloses the clinical application of GnRH analogues. The article discloses the use of these agonist drugs in successfully treating precocious puberty, prostatic cancer, breast cancer, female contraception, male contraception, endometriosis, uterine leiomyoma, and polycystic ovarian disease. However, although promising results in treating these various pathologies are disclosed, the need for effective LHRH antagonist is strongly emphasized.

LHRH antagonist drugs of the past have required extensive modifications in the native LHRH to obtain a potent antagonistic effect as compared to the relatively minor changes required for formulating superactive GnRH agonists. It has been believed that the number and the type of amino acid substitutions and the resulting conformation of the antagonist that affects LHRH receptor binding.

There is currently much research directed to the use of gonadotropic antagonists such as LHRH antagonists in treating pathological conditions which are normally responsive to a reduction in plasma levels of gonadotropic hormones such as uterine fibroids, precocious puberty, endometriosis and hormone dependent carcinomas. These antagonist peptides strongly inhibit LH secretion and have some effect, as explained above in diminishing FSH activity.

Well known examples of LHRH antagonists are those described by A. V. Schally and others in Proc. Natl. Acad. Sci. (USA), Vol 85, pp. 1637–1641 (1988). K. Folkers and others in Tetrahedron, Vol 46, pp. 33297–3304 (1990), also in Proc. Natl. Acad. Sci. (USA) Vol 85, pp. 8236–8240 (1988).

Although LHRH antagonists offer a promising alternative in treating hormone responsive disease, peptide antagonists synthesized so far have demonstrated serious deficiencies and side effects. Presently, sufficient potency has not been demonstrated in vivo, for the antagonistic peptides. Furthermore, serious side effects such as histamine release, anaphylactoid reactions, and hypotension occur. LHRH antagonists have also caused local vascular permeability changes and associated edematogenic effects, poor water solubility and inadequate duration of action.

What is needed is a water soluble LHRH antagonist peptide which exhibits sufficient potency so as to achieve an effective therapeutic effect, while minimizing anaphylactoid reactions of past antagonists described above.

SUMMARY OF THE INVENTION

Now in accordance with the present invention a luteinizing hormone releasing hormone, (LHRH) antagonist has been discovered which effectively reduces the amount of luteinizing hormone and follicle stimulating hormone produced by the anterior pituitary gland. The LHRH antagonist of the present invention reduces the level of circulating estrogen, progesterone and testosterone in mammals which are treated with a therapeutically effective dose of said antagonist.

The preferred embodiment of the LHRH antagonist peptide of the present invention is characterized by the following formula:

SEQ ID NO.: #1 wherein the Alanine residue at SEQUENCE position 1 is N-acetyl-D-3-(2-naphthyl)-Ala; the Phenylalanine residue at SEQUENCE position 2 is D-3-(4-chlorophenyl)-alanine; the Alanine residue at SEQUENCE position 3 is D-3(3-pyridyl)-Ala; the Lysine residue at Sequence position 6 is D-6-carbamoyl lysine; the Lysine residue at SEQUENCE position number 8 is Nε-isopropyl-Lys; and the Alanine residue at SEQUENCE position 10 is D-Ala-NH$_2$.

An alternative embodiment of the present invention is characterized by the following formula:

SEQ ID NO.: 2 wherein the Alanine residue at SEQUENCE position 1 is N-acetyl-D-3-(2-naphthyl)-Ala; the Phenylalanine residue at SEQUENCE position 2 is D-3-(4-chlorophenyl)alanine; the Alanine residue at SEQUENCE position 3 is D-3(3-pyridyl)-Ala; the Lysine residue at Sequence position 6 is D-6-carbamoyl lysine; the Lysine residue at SEQUENCE position number 8 is Nε-isopropyl-Lys; and the Proline residue at SEQUENCE position 9 is Pro-NHCH$_2$CH$_3$.

In another embodiment of the present invention a method for reducing circulating levels of estrogen, progesterone and testosterone is provided wherein an LHRH antagonist according to the present invention is administered to a subject mammal at a therapeutically effective dosage so as to reduce said levels. As is well known in the art, the therapeutically effective dosage for any given hormone antagonist is dependent on various factors identified with each subject to be treated such as subject weight, age, metabolic rate and plasma levels of gonadotropic hormones. However, the human dosage for the LHRH antagonists of the present invention generally ranges between about 0.1 and 1.0 mg/day in order to achieve a castration level of estradiol or testosterone.

The LHRH antagonist peptides of the present invention may be utilized as an alternative to ablation treatment in treating disease of estrogen and androgen responsive tissue which is ordinarily responsive to reduction of plasma levels of these hormones. When utilized for this purpose, individual subjects should be titrated to ablation levels of plasma testosterone or estrogen (estradiol). As discussed above, a daily dosage of from about 0.1 to 1.0 mg is used to achieve the required castration level.

DETAILED DESCRIPTION OF THE PREFERRED EMBODIMENTS

The LHRH antagonist peptides of the present invention may be utilized in the treatment of prostatic cancer. The antagonist is titrated to a dosage required to simulate castration levels in order to substantially reduce the circulating androgen level.

The peptides of the present invention may be utilized alone, or in combination with anti-androgens such as flutamide, cyproterone acetate, and ketoconazole. These anti-androgen preparations are required where significant androgen production occurs in the adrenal gland. Since adrenal production of androgens are not affected by LHRH anti-androgens may be combined with the peptides of the present invention in order to block androgen activity from adrenal origin.

The LHRH antagonist peptides of the present invention may be used as an alternative to ovariectomy in the palliative treatment of breast cancer of premenopausal women. Because of the relatively low level of estrogen in post menopausal women, and in women who have undergone ovariectomies, any reduction of this hormone through utilization of the LHRH antagonist peptide of the present invention would be of limited value.

The peptides of the present invention must be titrated so as to achieve profound pituitary and gonadal suppression. Such suppression occurs, as discussed above, with a daily average dosage range of about 0.1 to 1.0 mg/day.

The peptides of the present invention may be utilized in the treatment of endometriosis; the ectopic occurrence of endometrial tissue generally within the abdominal cavity. By suppressing gonadal steroid secretion, growth of endometrial tissue decreases to the level of atrophy, thus effectively reducing endometrial tissue island formation within the myometrium or in the pelvic cavity outside the uterus. Thus an alternative to anterior pituitary drugs such as Danazol (pregna-2, 4-dien-20-yno[2,3d]isoxazol-17-ol), and surgical excisions of implants through laparoscopy, in a method of treating endometriosis is provided wherein cardiovascular side effects and mild androgenic effects associated with such drugs are avoided, and the need for surgical excision is either eliminated or reduced.

The LHRH antagonist peptides of the present invention additionally provide a method for treating uterine leiomyoma in pre-menopausal women. By titrating patient estrogen levels to those levels found in post menopausal women, control of tumor growth, and regression is possible. Thus the peptides of the present invention provide an alternative to the only known (non-surgical) existing medical treatment of uterine leiomyoma; LHRH agonist therapy. Complete anterior pituitary suppression is required in order to ensure effective treatment of uterine leiomyoma.

The LHRH antagonist peptides of the present invention provide a method for treating polycystic ovarian disease. The increased androgen secretion associated with this disease may be associated with either ovarian or adrenal secretion. Since adrenal secretion is not responsive to variations in gonadotropic hormone levels, the LHRH antagonist of the present invention may alternatively be used as a diagnostic tool in differentiating the source of elevated plasma levels of androgen. By administering a castration level of the peptides of the present invention to a subject with polycystic ovarian disease, the level of androgen will profoundly decrease if ovarian tissue (LH-responsive tissue) is responsible for the unusually high levels of androgen. If, on the other hand, no substantial decrease in androgen level is detected, it is the adrenal gland which is responsible for the elevated androgen levels. If the ovarian tissue is responsible for elevated levels of androgen, the LHRH antagonist peptide of the present invention may be utilized, (at a castration level), in order to control polycystic disease and associated ache and hirsutism.

LHRH antagonist peptides of the present invention may be prepared utilizing automated peptide synthesis techniques well known to the art. The following examples disclose two methods utilizing standard techniques, however, one skilled in the art may readily adapt other techniques to different synthesizers.

EXAMPLE 1

A synthesis of an LHRH antagonist peptide according to the present invention was carried out by the solid-phase-method on a benzhydrylamine resin on a polystyrene support using the LABORTEC peptide Synthesizer (SP 650, LABORTEC AG, 4416-Bubendorf, Switzerland) using Fmoc-amino acids (FMOC=9-Fluorenylmethyloxycarbonyl) and following the manufacturers instructions.

Optionally Boc-amino acids,(Boc-t-butyloxycarbonyl) can be used. Both natural and unnatural amino acids were obtained by Bachem AG, Bubendorf, Switzerland. Purification of the crude peptide was accomplished by gel permeation chromatography on Sephadex G 25 followed by permeation chromatography on Sephadex G 25 followed by preparative HPLC purification on silica gel.

The following peptide was thus obtained. SEQ ID NO.: 1 wherein the Alanine residue at SEQUENCE position 1 is N-acetyl-D-3-(2-naphthyl)-Ala; the Phenyl-alanine residue at SEQUENCE position 2 is D-3-(4-chlorophenyl)-alanine; the Alanine residue at SEQUENCE position 3 is D-3(3-pyridyl)-Ala; the Lysine residue at Sequence position 6 is D-6-carbamoyl lysine; the Lysine residue at SEQUENCE position number 8 is N$\epsilon$-isopropyl-Lys; and the Alanine residue at SEQUENCE position 10 is D-Ala-NH2.

The molecular weight of the LHRH antagonist so synthesized is 1459.2 g/mol. The amino acid analysis yielded the following results: Serine 0.92, Proline 1.07, Alanine 0.98, Tyrosine 1.03. The product is freely soluble in water.

EXAMPLE 2

Utilizing substantially the same procedure as in Example 1, the following LHRH antagonist of the present invention was obtained. SEQ ID NO.: 2 wherein the Alanine residue at SEQUENCE position I is N-acetyl-D-3-(2-naphthyl)-Ala; the Phenylalanine residue at SEQUENCE position 2 is D-3-(4-chlorophenyl)alanine; the Alanine residue at SEQUENCE position 3 is D-3(3-pyridyl)-Ala; the Lysine residue at Sequence position 6 is D-6-carbamoyl lysine; the Lysine residue at SEQUENCE position number 8 is N$\epsilon$-isopropyl-Lys; and the Proline residue at SEQUENCE position 9 is Pro-NHCH$_2$CH$_3$.

EXAMPLE 3

The LHRH antagonist peptide of Example 1 was converted into a slightly soluble pamoate salt. An aqueous solution of the peptide of Example 1 was mixed with an aqueous solution of sodium pamoate. The resultant mixture was then filtered so as to allow collection of a sparingly soluble peptide pamoate salt which was thus formed.

EXAMPLE 4

The water soluble peptide of Example 2 was converted into a sparingly soluble stearate salt by mixing an aqueous solution of said peptide with an alcoholic (ethanol) solution of stearic acid and filtering the resulting stearate salt thus formed.

EXAMPLE 5

Six rats were utilized to test the LHRH antagonist peptide of Example 1 of the present invention for anaphylactoid properties. Each of the six rats was injected with 5 mg/kg of the test peptide. No mortality or other signs of anaphylactoid reactions were observed over a 24 hour period.

The effect of an LHRH antagonist peptide of Example 1 of the present invention was compared to the effect of "Antide", cf. A. Ljungqvist et al., Biochem. Biophys. Res. Comm., 148, 849–858 (1987)., an LHRH antagonist of the prior art. Both LHRH antagonists were intermuscularly injected into 6 rats at a dosage of 300 mcg/kg. The following results were obtained:

TABLE 1

| Group | 0 hr | 24 hr | 48 hr |
| --- | --- | --- | --- |
| Saline i.m. | 3.60 ± 2.04 | 2.74 ± 1.05 | 3.41 ± 2.14 |
| "Antide" 300 µg/kg i.m. | 3.35 ± 2.51 | 0.78 ± 0.37** | 1.96 ± 0.95 |
| Peptide of Example 1 300 µg/kg i.m. | 5.46 ± 3.32 | 0.067 ± 0.030*** | 0.84 ± 0.28* |

As can be seen by the above data in Table 1, the LHRH antagonist peptide of Example 1 is more than about ten times as effective as Antide, an LHRH antagonist of the prior art, at 24 hour suppression of plasma testosterone in rats. The data for 48 hours indicates the peptide of Example 1 is more than twice as effective as Antide.

For the intended therapeutic uses, the peptides of the invention are formulated in suitable pharmaceutical compositions, using well known techniques and excipients such as disclosed, for instance, in Remington's Pharmaceutical Sciences Handbook, Mack Pub. Co., N.Y. USA, XVII ed. The compositions of the invention will be preferably suited for the parenteral or intranasal delivery: for the parenteral administrations, pharmaceutical delivery systems consisting of a biodegradable and biocompatible polymer as a matrix are particularly preferred whereas for the intranasal delivery the combined use of pharmaceutically acceptable peptidase inhibitors and/or pharmaceutically acceptable mucosal penetration enhancers (surfactants, quaternary ammonium salts, betaine derivatives and the like) is preferred.

The daily dosage peptides will range from 0.1 to 1 mg of the peptides of the invention, suitably formulated.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

I claim:

1. A luteinizing hormone releasing hormone antagonist peptide whose structure is SEQ ID NO.: 1 wherein the Alanine residue at SEQUENCE position 1 is N-acetyl-D-3-(2-naphthyl)-Ala; the Phenylalanine residue at SEQUENCE position 2 is D-3-(4-chlorophenyl) alanine; the Alanine residue at SEQUENCE position 3 is D-3(3-pyridyl)-Ala; the Lysine residue at SEQUENCE position 6 is D-6-carbamoyl lysine; the Lysine residue at SEQUENCE position number 8 is Nε-isopropyl-Lys; and the Alanine residue at SEQUENCE position 10 is D-Ala-NH$_2$.

2. The peptide of claim 1 in the form of a pharmaceutically acceptable salt.

3. The peptide of claim 2 wherein said pharmaceutically acceptable salt is a pamoate or stearate salt.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ala  Phe  Ala  Ser  Tyr  Lys  Leu  Lys  Pro  Ala
1                  5                        10
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala  Phe  Ala  Ser  Tyr  Lys  Leu  Lys  Pro
1                  5
```